United States Patent [19]

Brown

[11] 4,332,612
[45] Jun. 1, 1982

[54] PLANT GROWTH PROMOTING COMPOSITION

[75] Inventor: Michael J. Brown, Randolph, N.J.

[73] Assignee: GAF Corporation, New York, N.Y.

[21] Appl. No.: 165,446

[22] Filed: Jul. 2, 1980

[51] Int. Cl.³ ............... A01N 43/36; A01N 55/00; A01N 31/00
[52] U.S. Cl. .......................... 71/95; 71/74; 71/76; 71/77; 71/79; 71/94; 71/118; 71/124
[58] Field of Search ............. 71/79, 76, 95, 124

[56] References Cited

U.S. PATENT DOCUMENTS

| | | | |
|---|---|---|---|
| 3,008,975 | 11/1961 | Schubert | 556/446 |
| 3,898,257 | 8/1975 | Gregory | 71/79 |
| 3,928,406 | 12/1975 | Leeper et al. | 71/79 |
| 3,985,780 | 10/1976 | Foery et al. | 71/79 |
| 3,997,595 | 12/1976 | Jung et al. | 71/86 |
| 4,191,555 | 3/1980 | Kliegman | 71/95 |

OTHER PUBLICATIONS

Kukalenko et al., "Pyrrolidinone ders, etc.," (1973) CA 79, No. 39335u, (1973).
Lorenz, "Acetylene Solution", (1952) CA 46, pp. 8355–8356 (1952).
Takahashi et al., "Long—lasting Pyrethkond etc.", (1975) CA 84 No. 85633r, (1976).
Fischer et al., "Herbicides", (1965) CA 64 p. 13321d, (1966).

Primary Examiner—Glennon H. Hollrah
Attorney, Agent, or Firm—James Magee, Jr.; Marilyn J. Maue

[57] ABSTRACT

The present invention relates to new compositions and methods for the regulation of plant growth, especially for prevention of lodging, promotion of fruit abscission, acceleration of ripening and sap flow, breaking of seed dormancy, advancement of sprouting, inhibition of germination and rhizome development or inhibition by utilizing a coacting mixture of a N-heterocyclic amide having one hetero-nitrogen atom per 5- or 6- membered ring and a haloalkyl silane having the formula:

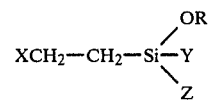

wherein
X is a chlorine, bromine or iodine atom;
Y and Z are each independently —OR; halogen; alkenyl of 3 to 8 carbon atoms or alkyl of 1 to 12 carbon atoms, both optionally substituted with halogen, lower alkoxy or phenyl; benzyl or phenyl, both optionally substituted with halogen, lower alkyl or lower alkoxy; and
R is hydrogen; alkenyloxy of 2 to 8 carbon atoms or alkyl of 1 to 12 carbon atoms, both optionally substituted with halogen, or alkoxy; benzyl or phenyl, both optionally substituted with halogen, lower alkyl or lower alkoxy and mixtures of said silanes and said amides.

15 Claims, No Drawings

PLANT GROWTH PROMOTING COMPOSITION

The silane compounds of the present invention are disclosed and discussed in U.S. Pat. Nos. 3,985,780; 3,008,975; and 3,928,406; the teachings of which are incorporated herein by reference. Certain of these haloalkyl silanes, employed in the compositions of the present invention, have displayed plant growth regulating activity superior to most commercially marketed regulants. However, many of these silanes are unstable, toxic or form toxic by-products upon hydrolysis. The silane esters are particularly unstable and are easily hydrolyzed to polysiloxanes and hydrohalic acid; whereas the silane dihalides are toxic agents and, although only slightly soluble in water, can be leached from the soil, contaminating ground water and streams. Furthermore, the doses required to achieve desired effects in plant growth regulation are sufficient to cause skin irritation and are lethal to certain fish and small animals; therefore, general use of these silanes is ecologically objectionable.

Accordingly, it is an object of the present invention to provide a composition which would enable use of certain silane compounds in ecologically acceptable concentrations without reducing the degree of plant growth regulation.

Another object of this invention is to extend the activity of silane compounds over a longer duration and/or to intensify plant growth regulating activity.

It is also an object of the present invention to provide an interacting, multicomponent composition for sustaining and regulating plant growth retardation or maturation response to said silane compounds, particularly beneficial in the treatment of seeds to prevent germination of weeds, to promote ripening of crops such as tomatoes, bananas, prunes, pineapples and tobacco, to increase sap flow in trees such as sugar maple and rubber trees, etc. to abscise fruit such as olives, peaches, apples, etc. and to defoliate harvestable crops such as cotton, beans and cucumbers and other crops which normally exhibit response to hormonal ethylene generation.

Another object is to provide for plant maturation while simultaneously reducing plant susceptibility to lodging.

Still another object is to provide an ecologically safe composition for the treatment of plants and an economical method for its application.

These and many additional objects and advantages will become apparent from the following description and disclosure.

According to this invention, there is provided an interacting mixture for preharvest or postharvest treatment of a plant, plant part or plant situs which comprises as active ingredients, an N-heterocyclic amide having one hetero-nitrogen and 4 or 5 carbon atoms in a 5- or 6- membered ring, such as for example, N-methylpyrrolidone, or mixtures of said N-heterocyclic monoamides, and a silane having the formula:

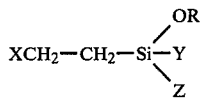

wherein

X is a chlorine, bromine or iodine atom;

Y and Z are each independently —OR; alkenyl of 3 to 8 carbon atoms or alkyl of 1 to 12 carbon atoms, both optionally substituted with halogen, lower alkoxy or phenyl; benzyl or phenyl, both optionally substituted with halogen, lower alkyl or lower alkoxy; and R is hydrogen; alkenyloxy of 2 to 8 carbon atoms or alkyl of 1 to 12 carbon atoms, both optionally substituted with halogen or lower alkoxy; benzyl or phenyl, both optionally substituted with halogen, lower alkyl or lower alkoxy, and mixtures of said silanes.

Examples of suitable N-heterocyclic amides include N-methyl-2-pyrrolidone, 2-pyrrolidone, N-methyl-2-pyridone, N-methyl succinimide and isomers and mixtures of these amides with other heterocyclic amides or with linear amides such as methyl substituted acetamides or formamides, e.g. N,N-dimethyl acetamide, N-methyl acetamide and N-methyl formamide. Of the active amide components, the tertiary heterocyclic amides are preferred and N-methylpyrrolidone is most preferred.

It has now been discovered that the addition of as little as about 20 ppm and as much as 50,000 ppm or more of the present N-heterocyclic amides to a composition containing 5–60% by weight of the silane in an inert carrier, enhances the activity of the silane by at least 15% up to 40% or more, so that smaller dosages, well within the limits of ecological safety specifications, can be employed to provide substantially the same degree of plant response as the previously employed silane formulations. Additionally, the duration of the regulating activity is significantly extended. The concentration of silanes in compositions of the prior art which have been usefully employed for agricultural purposes has been as low as 40 ppm and as high as 150,000 ppm depending upon whether a maturation or herbicidal plant response is intended and other conditions of application and species of plant.

With respect to the water-insoluble silanes, the complicated formulations required to form aqueous dispersions and emulsions can be greatly simplified by the addition of the present amides, particularly N-methyl-2-pyrrolidone, since the N-heterocyclic compounds, in addition to their coacting metabolic effects with silanes, contribute excellent solvent properties to improve plant penetration and distribution of the silanes in aqueous composition. Accordingly, individual adjuvants required for previous aqueous silane formulations, including surfactants, carriers, stabilizers, dispersants, thickeners, agglutinants and costly solvents, can be largely reduced or eliminated.

Normally, it would be expected that the addition of such heterocyclics, previously regarded as inert solvents, to a highly active plant growth promoter would have no promotional effect or any sustaining influence in growth regulation. Conversely, in the case of the present silanes, it is discovered that plant maturation effects are significantly extended and increased. Notwithstanding these promotion effects on the present silane compounds, the same heterocyclic amides provide no noticable improvement in the activity of the heterocyclic-substituted or alkinyl-substituted haloalkyl silane growth regulants. Also, polyvinylpyrrolidone has no promotion effect on the regulant properties of the present silanes. Accordingly, these silanes and polyvinylpyrrolidones are excluded from the mixtures of the present invention.

Suitable examples of silanes properly within the scope of this invention include the monobromo- and monochloro- methyl or ethyl silanes, such as 2-chloroethyl-tris(methoxyethoxy) silane
2-bromoethyl-tris(methoxyethoxy) silane
2-chloroethyl-tris(ethyloxyethoxy) silane
2-chloroethyl-tris(ethoxymethoxy) silane
2-bromoethyl-tris(ethyloxyethoxy) silane
2-chloroethyl-tris(methyloxyphenoxy) silane
2-chloroethyl-tris(butyloxyethoxy) silane
2-chloroethyl-tris(ethyloxyphenoxy) silane
2-chloroethyl-tris(octyloxy) silane
2-bromoethyl-tris(hexyloxy) silane
2-chloroethyl-tris(dodecyloxy) silane
2-chloroethyl-tris(propenyloxy) silane
2-chloroethyl-tris(butenyloxy) silane
2-chloroethyl-tris(3-chloro-2-butenyloxy) silane
2-chloroethyl-tris(2-chloropropyloxy) silane
2-chloroethyl-tris(3-phenylpropyloxy) silane
2-chloroethyl-tris(phenyloxy) silane
2-chloroethyl-tris(2-phenoxyethyl) silane
2-chloroethyl-tris(2-phenoxyethoxy) silane
2-chloroethyl-tris(2-benzyloxy) silane
2-bromoethyl-tris(2-benzyloxy) silane
2-chloroethyl-tris-(benzoxyethoxy) silane
2-chloroethyl-tris(4-chlorobenzyloxy) silane
2-chloroethyl-tris(4-methoxybenzyloxy) silane
2-chloroethyl-tris(2,4-dichlorobenzyloxy)silane
2-chloroethyl-tris(4-methoxyphenyloxy) silane
2-chloroethyl-tris(3-methylphenyloxy) silane
2-chloroethyl-tris(2,4-dimethylphenyloxy) silane
2-chloroethyl-tris(2-allyloxyethyl) silane
2-chloroethyl-bis(4-chlorophenoxy) methyl silane
2-chloroethyl-ethoxy-dichloro silane
2-chloroethyl-bis(ethoxy) methoxyethoxy silane
2-chloroethyl-bis(methoxyethoxy) ethoxy silane
2-chloroethyl-bis(hexenyl) ethoxy silane
2-chloroethyl-bis(ethoxy) ethyloxyethoxy silane
2-chloroethyl-bis(methoxy) ethoxyethoxy silane
2-chloroethyl-bis(hydroxy) ethyl silane
2-chloroethyl-bis(2-chloroethoxy) methyl silane
2-chloroethyl-bis(hydroxy) methyl silane
2-chloroethyl-bis(methoxy) methyl silane
2-chloroethyl-ethoxy-methoxy-2-chloroethoxy silane
2-bromoethyl-ethoxy-methoxy-2-chloroethoxy silane
2-bromoethyl-bis(2-chloroethoxy) ethyl silane
2-chloroethyl-ethoxy-methoxy-ethyl silane
2-chloroethyl-bis(benzyloxy) methyl silane
2-chloroethyl-bis(2,4-dibromobutyl) ethoxy silane
2-bromoethyl-bis(ethoxy) methyl silane
2-iodoethyl-bis(ethoxy) methyl silane
2-chloroethyl-bis(ethoxy) methyl silane
2-chloroethyl-bis(ethoxy) chloromethyl silane
2-bromoethyl-bis(ethoxy) chloroethyl silane
2-chloroethyl-tris(2-allyloxymethyl) silane
2-chloroethyl-tris(2-allyloxymethoxy) silane
2-chloroethyl-bis(propoxypropoxy) propyl silane
2-chloroethyl-bis(butoxymethoxy) ethyl silane
2-chloroethyl-bis(ethoxyethoxy)-2-chloroethoxy silane
2-bromoethyl-bis(ethoxyethoxy)-2-bromoethoxy silane
2-chloroethyl-bis(ethoxyethoxy) butyl silane
2-chloroethyl-bis(methoxyethoxy) methyl silane
2-bromoethyl-bis(ethoxymethoxy) methyl silane
2-bromoethyl-bis(methoxyethoxy) butyl silane
2-chloroethyl-bis(ethoxymethoxy) ethyl silane
2-chloroethyl-bis(ethoxyethoxy) benzyl silane
2-chloroethyl-bis(methoxyethoxy) phenoxy silane
2-chloroethyl-bis(phenoxy) methoxyethoxy silane
2-bromoethyl-bis(phenoxy) ethoxymethoxy silane
2-chloroethyl-bis(benzyloxy) ethoxyethoxy silane
2-chloroethyl-ethoxyethoxy silane dichloride
2-bromoethyl-ethoxyethoxy silane dibromide
2-chloroethyl-ethyloxyethoxy silane diiodide
2-bromoethyl-bis(allyloxy) methoxyethoxy silane
2-chloroethyl-bis(allyl) methoxyethoxy silane
2-chloroethyl-bis(2-chloroethyl) methoxyethoxy silane
2-chloroethyl-bis(2-chloroethyloxy) silane hydroxide
2-bromoethyl-bis(2-bromoethyl) methoxyethoxy silane
2-bromoethyl-bis(2-bromoethoxy) silane hydroxide
and isomers and mixtures of the above compounds.

Of the present silanes, the 2-chloroethyl silanes containing at least two —OR groups are preferred, and the 2-chloroethyl tris(OR) silanes are most preferred. Addition of the present amides to compositions containing the silanes increases maturation over that normally obtained or obtained with the individual haloethyl silane alone. The present mixtures, particularly those containing silanes having the formula:

$$\text{Halo—CH}_2\text{—CH}_2\text{—Si(oxyalkyloxyalkyl)}_3,$$

induce maturation effects on yound and fully developed plants, harvested crops or plant seeds; although it will be understood that the degree and type of plant response is also influenced by the amount of heterocyclic amide and concentration of the mixture employed, the species of plant and the climatic conditions at the time of application.

Although certain silanes induce shorter internode response, promote abscission of fruits and leaves, induce latex and sap flow and advance seed germination and grain ripening, they also produce some undesirable side effects, particularly in plants of the Gramineae family, among which are malformation and/or underdevelopment of seedheads so that certain grasses treated with these compounds may loose their ability to germinate or suffer browning, blanching or chlorosis of leaves or interruption of rhizome development. However, by supplementing a portion of the effective amount of silane with the present N-heterocyclic amides, smaller non-harmful amounts of silane can be employed while still maintaining high activity for beneficial effects and, in several cases, surpassing the activity of the silane for the desired effects while minimizing or completely eliminating the undesirable side effects.

According to this invention, mixtures of the present N-heterocyclic amide and the silane in a mole ratio of between about 0.15:1 and about 5:1 are successfully applied to reduce the rate of stem elongation in the treatment of corn, oats, rye grass, zoysia, bent grasses, Bermuda grass, Kentucky bluegrass, fescue and other turf grasses by 20-40%. Shorter plants of a more branched and/or rhizomed structure are developed, thus maintaining the plant's ability to propagate either through rhizome generation or seed germination. An additional advantage is realized in that the present mixture can be applied to fully-matured plants without the harmful effects discussed above. Seedling plants are generally more tolerant of harmful chemicals than are fully-matured plants which have lost substantial degree of cell differentiation present in the previous stages of development. Thus, while several plant growth regulants have been effectively employed to slow the growth of seedling turf grasses, they are not practical for application over an extended period on established, fully matured plants. Particularly beneficial mixtures of the invention for inhibition of the growth rate of grasses include chloroethyl-tris(ethoxymethoxy) silane/N-methyl-2-pyrrolidone, 2-chloroethyl-tris(ethoxyethoxy) silane/N-methyl-2-pyrrolidone and 2-chloroethyl-tris(methoxyethoxy) silane/N-methyl-2-pyrrolidone in a mole ratio of between about 1:2 and about 2:1; although it is to be understood that other mixtures implied in the foregoing disclosure can also be employed for the treatment of Graminae to obtain the above cited benefits.

Separate 50-plant plots, containing rye grass, Johnson grass, zoysia and winter wheat, all at the second foliate stage, sprayed to run off with 1,000–4,000 ppm of aqueous solutions of the specific, particularly beneficial mixtures noted above, result in significant decrease in the average rate of stem elongation up to 3 months after treatment. The mixture-treated plants achieve 100% normal rhizome development and are free of phytotoxic effects, such as chlorosis and blanching. The absence of shoot-tip dieback and abortion or malformation of grass seedheads are also beneficial effects achieved with the present mixtures.

While the above described mixtures can be applied in an undiluted state, for economic considerations and for more uniform distribution, it is desirable to incorporate the mixture in a dry powder, granules, paste or liquid carrier suitable for dusting, spraying, smearing, washing, dipping or broadcasting over a growing crop area or over the soil in which seeds have been or will soon be deposited.

Generally, the proportion of heterocyclic amide to silane employed in the present invention can be varied within the range of between about 0.05:1 and about 5:1. This mixture can be directly dispersed in water or it can be uniformly mixed with a carrier such as a liquid solvent, emulsifier or dispersant or an inert particulate solid or a heavy oil or grease, and applied to the plant, plant part or plant situs as a spray, dust, paste, etc. Suitable dry carriers which may be employed include particles varying in fineness from granules to dusts, such as, talc, bentonite clays, diatomaceous earths, sand, charcoal dust, kaolin, chalk, limestone, sawdust, ground nut shells or any of the other conventionally employed agricultural dry particulate extenders. Examples of liquid carriers include benzene, methyl or chloro substituted benzenes, cyclohexane, liquid hydrocarbon paraffins, alkylnaphthalenes, mineral or vegetable oils, petroleum oil fractions, fatty acid alcohols, low molecular weight ketones, water or any combination of the above named liquid/liquid or solid/liquid carriers which are compatible and inert with respect to the present plant growth regulating mixture.

In most cases the silane halides of the present invention have only a very limited solubility in water. For these halides an additional advantage is realized in that the present heterocyclic amides serve as emulsifiers and surfactants for the silanes in aqueous solution without the addition of extraneous chemicals. Although formulations containing substantial amounts of these adjuvants can be used if desired, they are usually superfluous except in certain instances where a high excess of the silane component in a concentrated active mixture is employed, e.g. greater than a 3 molar excess. In the later case, between about 5% and about 25% by weight emulsifier or surfactant can be added to the formulation when an aqueous solution, dispersion, suspension or emulsion is desired.

Other adjuvants may be incorporated or formulated with the present mixture, depending upon the demands of a particular application. For example in areas of high rainfall, it may be desirable to include a thickening agent, such as for example any of the conventionally employed gums or resins, including locust bean gum, guar gum, low molecular weight polymers, or vegetable oils such as palm oil, coconut oil or greases. Adjuvants in amounts up to 10% or more of the total formulation can be employed, if desired.

Additional adjuvants, which may be added or formulated with the present mixtures in a carrier, include conventional fungicides, and pesticides and/or other plant growth regulants which do not materially alter the plant growth regulating properties of the present silane/amide mixtures.

Desirably, the mixtures of the present invention with the inert carrier, optionally containing other adjuvants, are applied to plants, a plant part or plant situs in a concentration between about 30 ppm and 100,000 ppm. Generally, for effects such as seed germination, resistance to lodging and increased sap flow, concentrations of between about 50 and about 5,000 ppm are adequate; whereas for fruit ripening and inhibition of sucker development, concentrations between about 3,000 and about 15,000 ppm are suitable. For defoliation and fruit thinning, concentration in the order from about 6,000 to about 100,000 ppm are advantageously employed.

The formulations or compositions of the present invention can be prepared by any one of several convenient methods. For example, the silane and the N-heterocyclic amide can be separately dissolved in, or admixed with, the same or different solvents or carriers and then combined before applying to the plant, plant part or plant situs or the components in the same or individual carriers can be combined upon application to the plant. Alternatively, both components can be simultaneously or sequentially dissolved in, or admixed with the same carrier or solvent and cosolvent to provide the desired composition. Adjuvants can be added to either component-carrier composition, before or after combination of the components. In certain instances it may be desirable to form a composition with a liquid carrier for one of the components, e.g., an aqueous solution of N-methylpyrrolidone, and a second composition with a dry carrier for the silane component, after which the components may be mixed, before or upon application on the plant, to form a viscous liquid or a paste which is resistant to removal by rain or such subsequent treating operations as the consumer may require, e.g., the subsequent application of fungicide, a selective herbicide, a pesticide or other chemical spray.

The triester haloalkyl silanes of the present invention are relatively unstable in aqueous solutions; although the present amides extend the stability of these compounds. Previously, granular or anhydrous liquid solutions or suspensions were recommended unless the composition was prepared for immediate use. A convenient and practical method for utilization of the present triesters involves the use of a sprayer/mixer adapted for attachment to a water hose and including a water nozzle mixer head, a sealed reservoir containing the present silane/amide mixture concentrate solution in a non-aqueous water soluble carrier and a hollow suction tube connecting and in open communication with the water spray nozzle head and the bottom portion of the reservoir containing the active mixture concentrate, said tube being of a dimension adapted to respond to suction created by the passage of water through the nozzle head and to pass said concentrate from the reservoir into the nozzle head for mixture with water before exiting from the nozzle as an aqueous spray. The concentration of the mixture is preadjusted so that the desired concentration in aqueous solution will be attained in the nozzle head before or upon ejection from the spray nozzle. It is also to be understood that the components of the active mixture can be separately applied, e.g. as atomized sprays, in the same or individual carriers so as to form the mixture upon condensation on or contact with the plant surface.

As stated above, the present mixtures provide various plant growth effects. In the case of soybeans and cereal grasses, the present mixtures promote shorter sturdier stems and offer extended protection against lodging. Below 10,000 ppm concentration, these mixtures generally prevent excessively rapid defoliation so as to conserve transpiration as the underdeveloped crop matures to harvestability. To obtain these beneficial effects, preferably between about 100 and about 5,000 ppm of a 1:2 to 2:1 molar mixtures of N-methyl pyrrolidone/silane such as 2-chloroethyl-tris(methyloxyethoxy) silane, 2-bromoethyl-tris(methyloxyethoxy) silane, 2-chloroethyl-tris(ethyloxyethoxy) silane or other silanes, recited herein is sprayed to drench on wheat plants in the fifth trifoliate leaf stage. Omission of N-methylpyrrolidone in the composition results in rapid defoliation before 80% of the crop has reached maturity and taller, thinner plant stems are produced which result in a significant increase in lodging. The present admixtures overcome lodging and delay defoliation by several days while advancing the crop to ripeness at least 4 to 5 days sooner than untreated crop. The same effect is obtained when the above mixtures are applied to cotton.

As an example of ripening of picked fruit, about 4,500 ppm N-methyl-pyrrolidone is added to each of 4,500 ppm aqueous solutions of 2-chloroethyl-tris(methyloxyethoxy) silane, 2-bromoethyl-tris(methoxyethoxy) silane or 2-chloroethyl-tris(ethyloxyethoxy) silane. A fourth aqueous solution containing 900 ppm 2-chloroethyl-tris(methyloxyethoxy) silane omitting N-methyl pyrrolidone is also prepared. Three green picked bananas from the same stalk are immersed in each of the four solutions for a period of 35 minutes. The fruit treated with the solution free of N-methylpyrrolidone, i.e., the fourth solution, yellows 5 days before untreated fruit; whereas the bananas treated with the remaining three solutions yellow 6 to 7 days before untreated fruit.

When used alone, the N-heterocyclic compounds of the present invention behave as ethylene inhibitors as shown by the following examples 1–19 and fruit yellowing is significantly delayed 1 or 2 days after normal yellowing. Accordingly, it is all the more surprising that these compounds in admixture with the silanes, induce a promotional ripening effect in excess of that obtained with the unmixed silane compositions. In the following Examples 1–19 of Table I, the ethylene inhibiting effect of various N-heterocyclic amides is measured and reported.

EXAMPLES 1 THROUGH 19

In a growth chamber maintained at 30° C. and 2,000–3,000 foot candle light, soybean plants from the same seed source were grown to various stages of development. Each of the following experiments were carried out in quadruplicate, and the results (found to be highly reproducible), were averaged and reported in Table I below.

In the following Examples 1–19, leaf disc samples from (a) plant seedlings about 2 weeks old (Examples 1–4); (b) underdeveloped plants at the trifoliate stage (Examples 5–8); (c) fully-developed plants with no further growth increase (Examples 9–12); (d) a second group of fully developed plants (Examples 13–16); and (e) a third group of fully developed plants (Examples 17–19), were removed by cutting the leaf with a circular cork borer. Each leaf disc sample was immersed for 30 minutes in a 100 milliliter aqueous solution containing water as a control or aqueous solutions containing 1,000 ppm and 3,000 ppm of the compound to be tested. At the end of 30 minutes the leaf disc was removed from its solution, patted dry and inserted into a 25 ml glass vial equipped with a septum through which a syringe could be inserted for extracting a sample of the supernatant air above the leaf disc. Examples 1 through 16 were allowed to stand in the light for one hour and Examples 17 through 19 were allowed to stand in the light for 16 hours, after which a gas sample above the leaf in the vial was removed and analyzed for ethylene by gas liquid phase partition chromatography. Comparison with the control, reported in nanoliters of ethylene per liter of air per 10 $cm^2$ of leaf surface, are presented in the following Table (based on an average of 4 replicate samples). For the purpose of comparison, the control was assigned a value of 1.0 and the test compounds were reported as the percent deviation from the control.

Each of the foregoing experiments was repeated, except that the leaf disc samples were similarly treated and held in the dark for the above period prior to analysis of the gas samples. The results of these experiments are also reported in Table I.

TABLE I

| Ex. No. | TEST COMPOUND | $C_2H_4$ GENERATED-BASED ON CONTROL | | | |
|---|---|---|---|---|---|
| | | 1000 ppm | | 3000 ppm | |
| | | Light | Dark | Light | Dark |
| 1. | Control(water) = 500 nl $C_2H_4$/1/10$cm^2$ | 1.0 | 1.0 | 1.0 | 1.0 |
| 2. | N-(hydroxyethyl)-2-pyrrolidone | −38% | −25% | −45% | −32% |
| 3. | 2-Pyrrolidone | −73% | −69% | −78% | −75% |
| 4. | N-methyl-2-pyrrolidone | −84% | −82% | −91% | −91% |
| 5. | Control(water) = 640 nl $C_2H_4$/1/10$cm^2$ | 1.0 | 1.0 | 1.0 | 1.0 |
| 6. | N-methyl-2-piperidone | −38% | −60% | +150% | +110% |
| 7. | N-methyl-2-pyridone | −50% | −55% | +130% | +115% |
| 8. | N-methyl-2-pyrrolidone | −50% | −65% | −65% | −90% |
| 9. | Control(water) = 640 nl $C_2H_4$/1/10$cm^2$ | 1.0 | 1.0 | 1.0 | 1.0 |
| 10. | N-(hydroxyethyl)-2-pyrrolidone | −15% | +120% | +185% | +250% |
| 11. | 2-Pyrrolidone | −40% | −24% | +120% | +166% |
| 12. | N-methyl-2-pyrrolidone | −50% | −50% | −61% | −60% |

TABLE I-continued

| Ex. No. | TEST COMPOUND | C$_2$H$_4$ GENERATED-BASED ON CONTROL | | | |
|---|---|---|---|---|---|
| | | 1000 ppm | | 3000 ppm | |
| | | Light | Dark | Light | Dark |
| 13. | Control(water) = 640 nl C$_2$H$_4$/1/10cm$^2$ | 1.0 | 1.0 | 1.0 | 1.0 |
| 14. | N-methyl-2-pyrrolidone | −50% | −60% | −20% | −40% |
| 15. | N-(methyl)-2-piperidone | +40% | −50% | +190% | — |
| 16. | N-methyl-2-pyridone | −80% | −50% | −40% | +170% |
| 17. | Control(water) = 500 nl C$_2$H$_4$/1/10cm$^2$ | 1.0 | — | 1.0 | — |
| 18. | 2-Pyrrolidone | −40% | — | +104% | — |
| 19. | N-methyl-2-pyrrolidone | −50% | — | −46% | — |

It is noted that certain of the heterocyclic agents in the above table provide an ethylene generating effect at the higher 3,000 ppm concentration and that this effect occurs in older plant tissue which has less tolerance for excessive amounts of certain N-heterocyclic amides and therefore an increase marked by the generation of ethylene is observed as the response to a stress effect induced by the chemical. In these cases, it is also noted that the agent generally reaches an efficacy threshold at a concentration less than 3,000 ppm, e.g. 1,000-2,800 ppm. Specifically, at between about 1,800-2,400 ppm, a maximum response is obtained and amounts in excess of about 2,500 ppm are unable to provide additional inhibition of ethylene; in fact, concentrations of 3,000 ppm often induce a stress situation where the opposite result, namely increased ethylene generation, is observed. Accordingly, with the exception of 2-pyrrolidone and N-methyl pyrrolidone, the selection of the amide component in the present mixture is partly dependent on the age of the plant.

Notwithstanding, the above ethylene inhibitory properties of the present amides, when combined with silanes of this invention, they perform in a manner such that plant growth promotion or plant maturation is intensified and extended. In the case of the 2-haloethyl-tris(alkoxyalkoxy) silanes, defoliation, fruit abscission, fruit ripening and increase of sap flow are obtained as a result of increased ethylene generation. Intensification of these effects by the addition of the present amides is believed attributable to an interaction with the silane rather than the independent action of two plant growth regulating compounds whose individual effects would appear to neutralize each other.

Having thus generally described the present invention, reference is now had to the examples which illustrate preferred embodiments but which are not to be construed as limiting to the scope thereof as more generally described above and as defined in the appended claims. All amounts and proportions in the following examples are by weight unless otherwise indicated.

EXAMPLE 20

The increased activity of the 2-haloethyl-tris(alkyloxyalkoxy) silanes is illustrated in the abscission of apples from trees treated by spraying to drench with a mixture of 2,000 ppm N-methyl-2-pyrrolidone/2,000 ppm 2-chloroethyl-tris(methyloxyethoxy) silane in aqueous solution by use of a mixer-sprayer. Ten days after treatment, a pull force of only 10 oz. is required to separate the fruit from the tree as compared with, 12 days after treatment, 30 oz. and 12 oz. pull force for 4,000 ppm and 2,000 ppm of 2-chloroethyl-tris(methyloxyethoxy) silane alone and 100 oz. pull force for untreated trees. Ten days after the spraying treatment with 2,000 ppm of 2-chloroethyl-tris(methyloxyethoxy) silane resulted in a pull force of 15 oz. Normal fruit drop from untreated trees occurs 8 days later than the trees treated with the unmixed silane spray.

The same increased abscission of the present amide/silane mixture, by disorganization of tissue between the terminal pedicel and the fruit, is obtained with all citrus fruit trees as well as walnut, almond, prune, olive, peach and pear trees when treated in accordance with this example. The same increased abscission is also obtained when 2-chloroethyl-tris(ethoxyethoxy) silane, the corresponding 2-bromoethyl-tris(ethoxyethoxy) silane or 2-iodoethyl-tris(ethoxyethoxy) silane or other 2-haloethyl tris(lower alkoxy lower alkoxy) silanes are substituted in the above composition.

EXAMPLE 21

One group of five 14-week old hirsuiti cotton plants, normally undergoing 60% defoliation in the course of maturation to harvest, are drenched with an aqueous solution containing 12,000 ppm of 2-chloroethyl-tris(ethoxyethoxy) silane and a second group of five 14-week old hirsuiti cotton plants are drenched with an aqueous solution containing a mixture of 4,000 ppm N-methyl-2-pyridone and 4,000 ppm of said silane. The amide free group of five 14-week old hirsuiti cotton plants are drenched with an aqueous solution containing a mixture of 4,000 ppm N-methyl-2-pyridone and 4,000 ppm of said silane. The amide free silane solution results in 70-75% defoliation 8 days after spraying; whereas the solution of the present mixture results in 80-85% defoliation 8 days after spraying.

When N-methyl-2-pyrrolidone is substituted in the above mixture, 85-90% defoliation of the cotton plants is achieved. Similar results are obtained when 2-chloroethyl-bis(ethoxymethoxy) ethoxy silane or the corresponding 2-bromoethyl or 2-iodoethyl derivatives are substituted in the above mixture.

It is also noted that cotton, tomato and pea plants sprayed with these mixtures have a shorter more branching structure offering more crop sites than the corresponding untreated or silane treated plants.

EXAMPLE 22

Promotion of seed germination with the present mixture is generally effected at lower dosage levels, e.g. 25 to 550 ppm of mixture wherein amide: silane mole ratio is between about 0.05:1 and about 1:1. Specifically, 100 ppm aqueous solutions of 2-chloroethyl-bis(3-chloro-2-butenyl)-3-chloro-2-butenyloxy silane and a mixture of said silane with 2-pyrrolidone in a 1:0.25 mole ratio are compared for promotion of wheat seed germination, under controlled temperature and humidity, after treating the soil of 2 separate plots containing 100 seeds each with 0.5 liter of each solution. After 10 days, an untreated control plot provides only 25% germination; as compared with 80% for the silane treated plot and 85% for the plot treated with the present mixture. Similar results are obtained when N-(hydroxyethyl)-2-pyrrolidone, N-methyl-2-pyrrolidone or N-methyl-2-piperidone are substituted for 2-pyrrolidone in this example. Also other silanes, such as for example, 2-chloroethyl-bis(ethyloxyethoxy)-2-chloroethyl silane, 2-chloroethyl-bis(ethyloxy)ethoxyphenoxy silane, 2-chloroethyl-bis(benzyloxy)-ethoxy silane, 2-chloroethyl-bis(ethoxymethoxy) silane chloride, 2-chloroethyl-bis(methyloxyethoxy)-allyl silane, etc. or the corresponding bromo or iodo derivatives can be substituted for the silane in this example to provide accelerated seed germination.

EXAMPLE 23

Diagonal strips around the trunk of 5 fully-grown sugar maple trees are cut for collecting sugar maple sap. A viscous (25% toluene/75% olive oil) solution containing 10% 2-chloroethyl-tris(4-methoxyphenyloxy) silane and a similar solution containing a 10% mixture of N-methyl-2-pyrrolidone and said silane in a mole ratio of 1:5 are individually smeared above and below the stripped portion of each of 2 trees; one tree being left untreated as a control.

Six weeks after the applications, the excreted sap per tree is collected and weighed. The two trees treated with silane free of amide average 0.74 grams of sap; as compared to the averaged 0.80 grams of sap collected for the amide/silane mixture-treated trees and 0.5 grams of sap collected from the untreated tree. Similarly, latex flow is increased when treating rubber trees with the above mixture or with mixtures wherein other silanes have been substituted, e.g. 2-chloroethyl-tris(ethyloxyphenoxy) silane, 2-chloroethyl-tris(4-chlorobenzyloxy) silane and 2-chloroethyl-bis(benzyloxy) ethoxyethoxy silane.

EXAMPLE 24

The ripening of three groups of 12 green fully developed New Yorker tomatoes, randomly picked from tomato plants grown in a greenhouse under similar growth conditions are compared after the following treatment. One group is immersed in a 10% aqueous MEK solution containing 3,000 ppm of a 1:1 molar mixture of N-methyl-2-pyrrolidone and 2-chloroethyl-tris(4-methoxybenzyloxy) silane for 1.25 hours and then dried. A second group of 12 tomatoes is immersed for the same period in a solution containing 3,000 ppm of the same silane in the absence of N-methyl pyrrolidone, and a third group of 12 tomatoes is left untreated as a control. The tomatoes of all three groups are then placed on trays and observed every 3 days for signs of reddening. After 9 days, 75% of the tomatoes treated with the present active mixture attain a bright red color, as compared with 65% for the silane-treated plants and only 47% for the control. After 12 days, 85% of the mixture-treated tomatoes are bright red, as compared with 70% of the silane-treated tomatoes and only 65% for the untreated tomatoes.

The same fruit ripening response is obtained when 2-chloroethyl-tris(4-chlorobenzyloxy) silane, 2-chloroethyl-bis(4-methoxyphenoxy)ethoxy silane or 2-chloroethyl-bis(3-chloro-2-butenyloxy)butoxy silane is substituted in the mixture of this example or when one or more of said substitute silanes supplement the silane portion in the mixture of this example.

EXAMPLE 25

Green tomato fruit from Pixie Hybrid tomato plants grown in the greenhouse were treated with aqueous spray solutions which contained the indicated concentrations of 2-chloroethyl-bis(ethyloxy)methyloxy silane and compositions thereof. The plants were sprayed at a temperature 85° F. under a 12-hour light period. The evaluations are summarized in following Table II.

TABLE II

| Treatment | Conc. ppm | Avg. No. of Days from Treatment Until Pink | % Defoliation |
|---|---|---|---|
| Control | 0 | 19 | 0 |
| 2-chloroethyl-bis(ethoxy)methoxy silane | 18,000 | 10 | 4 |
| 2-chloroethyl-bis(ethoxy)methoxy silane + maleic hydrazide (1:1 molar mixture) | 18,000 | 16 | 10 |
| 2-chloroethyl-bis(ethoxy)methoxy silane + N-methyl-2-pyrrolidone (1:1 molar mixture) | 18,000 | 8 | 2 |

The above results indicate that whereas the maleic hydrazide mixture decrease the rates of fruit ripening and promotes defoliation of the tomato plants, the present monoamide mixture enhances the ripening activity of the silane while significantly reducing undesirable defoliation.

The same differences between the present N-heterocyclic monoamide and maleic hydrazide in plant response to silane compounds are observed in the flowering of pineapples, i.e. the present amides advance the promotional flowering properties of the silanes whereas maleic hydrazide inhibits normal flowering and significantly reduces the promotional flowering properties of the silanes.

In the present example, other silane compounds can be substituted in the mixture with N-methyl-2-pyrrolidone, e.g. 2-chloroethyl-tris(ethoxyethoxy)silane, 2-chloroethyl-tris(methoxyethoxy) silane, 2-chloroethyl-bis(ethoxymethoxy)-2-chloroethoxy silane, etc. to provide the same beneficial effects. Also, 2-pyrrolidone or N-methyl-2-pyridone can be substituted in whole or in part for N-methyl-2-pyrrolidone in this example to advance fruit ripening of the silane.

EXAMPLE 26

Twenty peach trees of the Redglobe variety, sprayed after fruit set with an aqueous 100 ppm solution of N-methyl-2-pyrrolidone/2-chloroethyl bis(benzyloxy)-methyl silane in a 1:1.2 molar ratio at a rate of 200 gallons per acre (Group A); twenty Redglobe trees similarly sprayed with an aqueous 100 ppm solution of said silane (Group B); and twenty Redglobe trees similarly sprayed with an aqueous 100 ppm solution of ethephon (Group C), compared for efficacy in fruit thinning, demonstrate the superiority of the present mixture as shown in Table II. Spraying is carried out at a temperature of about 80° F. and about 65% humidity.

Another 20 peach trees of the same variety at the same stage of development and growing under substantially the same conditions were left unsprayed as a control (Group D).

TABLE III

| Treatment | % Fruit Drop Days After Spraying 4 | 8 | % Defoliation 8th Day | % Reduction in Fruit Size |
| --- | --- | --- | --- | --- |
| Group A | 55 | 95 | 10 | 2 |
| Group B | 55 | 90 | 15 | 10 |
| Group C | 30 | 80 | 12 | 5 |
| Group D | 0 | 40 | 2 | 0 |

The above results establish that the present mixture is a highly effective chemical thinning agent. The present mixture is also an effective harvesting aid when applied after fruit ripening in concentrations as low as from about 50 to about 125 ppm.

Other silanes which can be substituted for the 2-chloroethyl-bis(benzyloxy)methyl silane in the mixture with N-methyl-2-pyrrolidone to provide the above benefits include 2-chloroethyl-bis(hydroxy)ethoxy silane, 2-chloroethyl-bis(ethoxyethoxy)hydroxy silane, 2-chloroethyl-ethoxymethoxy silane dichloride, 2-chloroethyl-bis(methoxyethoxy) silane chloride and the brominated derivatives thereof.

It is to be understood that the above examples are merely representative of the mixtures which can be employed in accordance with the present invention and that any of the foregoing silanes or N-heterocyclic amides defined within the scope of this invention can be substituted in these examples to obtain the benefits described therein.

What we claim is:

1. A plant growth promoting composition consisting essentially of an effective amount of the mixture of N-methylpyrrolidone, and a silane having the formula:

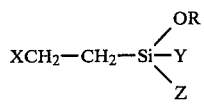

wherein

X is a chlorine, bromine or iodine atom;

Y and Z are each independently —OR; halogen; alkenyl of 3 to 8 carbon atoms or alkyl of 1 to 12 carbon atoms, both optionally substituted with halogen; and R is hydrogen; alkenyl of 2 to 8 carbon atoms optionally substituted with halogen; alkyl of 1 to 12 carbon atoms optionally substituted with halogen, phenoxy or lower alkoxy;

benzyl or phenyl, both optionally substituted with halogen, lower alkyl or lower alkoxy, said N-heterocyclic amide and silane being combined in a mole ratio between about 0.05:1 and about 5:1.

2. The composition of claim 1 wherein at least one of Y and Z of the silane component is an —OR radical, wherein R is alkoxyalkylene, alkoxyphenylene, alkyl or benzyl.

3. The composition of claim 2 wherein Y and Z of said silane are alkoxyphenoxy groups.

4. The composition of claim 1 wherein Y and Z are benzyloxy radicals.

5. The composition of claim 1 wherein X of said silane is chloro.

6. The composition of claim 2 wherein R is alkoxyalkylene.

7. The composition of claim 6 wherein Y and Z of said silane are —OR groups.

8. The composition of claim 1 wherein at least one of Y and Z of said silane is a chlorine atom.

9. The composition of claim 1 wherein Y and Z of said silane are hydroxy groups.

10. The composition of claim 1 wherein Y and Z of said silane are haloalkenyl groups.

11. The composition of claim 1 wherein the mixture is N-methyl-2-pyrrolidone and 2-chloroethyl-tris(alkoxyalkoxy) silane and the alkoxyalkoxy radicals contain 1 or 2 carbon atoms.

12. The composition of claim 1 wherein the mixture is N-methyl-2-pyrrolidone and 2-chloroethyl-tris(methyloxyethoxy) silane.

13. The composition of claim 1 wherein the mixture is N-methyl-2-pyrrolidone and 2-chloroethyl-bis(benzyloxy) methyl silane.

14. The process of contacting a plant, plant part or plant situs with a plant growth promoting amount of the composition of claim 1.

15. The process of claim 14 wherein the composition is employed in an inert carrier and wherein the concentration of the composition in said carrier is between about 30 ppm and about 100,000 ppm.

* * * * *